United States Patent
Kulkarni et al.

(10) Patent No.: US 6,482,987 B2
(45) Date of Patent: Nov. 19, 2002

(54) PHARMACEUTICAL COMPOSITION CONTAINING BUPROPION HYDROCHLORIDE AND A STABILIZER

(75) Inventors: Prakash Shriram Kulkarni, Parsippany, NJ (US); Bharat Bhogilal Shah, Ridgefield, NJ (US); Amitava Maitra, Sayreville, NJ (US); Joseph Michael DeVito, Middletown, NY (US)

(73) Assignee: Clonmel Healthcare, Ltd., Tipperary (IE)

( * ) Notice: Subject to any disclaimer, the term of this patent is extended or adjusted under 35 U.S.C. 154(b) by 58 days.

(21) Appl. No.: 09/824,371

(22) Filed: Apr. 2, 2001

(65) Prior Publication Data

US 2001/0021721 A1 Sep. 13, 2001

Related U.S. Application Data

(62) Division of application No. 09/000,999, filed on Dec. 30, 1997, now Pat. No. 6,221,917.

(51) Int. Cl.⁷ .............................................. C07C 225/00
(52) U.S. Cl. ...................... 564/345; 564/343; 424/468; 424/482
(58) Field of Search ................................ 424/468, 482; 564/343, 345

(56) References Cited

U.S. PATENT DOCUMENTS

| | | | |
|---|---|---|---|
| 3,819,706 A | 6/1974 | Mehta et al. | 564/345 |
| RE33,994 E | 7/1992 | Baker et al. | 424/465 |
| 5,358,970 A | 10/1994 | Ruff et al. | 514/644 |
| 5,427,798 A | 6/1995 | Ludwig et al. | 424/464 |
| 5,731,000 A | 3/1998 | Ruff et al. | 424/451 |

OTHER PUBLICATIONS

Osol. et al., Remington's Pharma. Sci., 15th Ed., 1586–1587 (1976).

*Primary Examiner*—Dwayne C. Jones
(74) *Attorney, Agent, or Firm*—Wyeth Ayerst

(57) ABSTRACT

Novel, stable formulations of bupropion hydrochloride are provided which will maintain at least 80% of initial bupropion hydrochloride potency after one year. Methods of inhibiting degradation of bupropion hydrochloride and methods of preparing stable formulations of bupropion hydrochloride are also provided.

2 Claims, No Drawings

PHARMACEUTICAL COMPOSITION CONTAINING BUPROPION HYDROCHLORIDE AND A STABILIZER

This application is a divisional application of Ser. No. 09/000,999, filed Dec. 30, 1997, U.S. Pat. No. 6,221,917.

BACKGROUND OF THE INVENTION

Bupropion hydrochloride is a common antidepressant sold in immediate release, modified release, and extended release tablet forms. See U.S. Pat. Nos. 3,819,706 and 3,885,046. As with many pharmaceuticals, the stability of bupropion hydrochloride is affected by a number of factors including formulation microenvironments and storage conditions.

One formulation of bupropion hydrochloride is taught by Ruff et al., U.S. Pat. No. 5,358,970 to prevent or inhibit degradation of bupropion hydrochloride using one of the stabilizers L-cysteine hydrochloride, glycine hydrochloride, malic acid, sodium metabisulfite, citric acid, tartaric acid and L-cystine dihydrochloride. These solid dosage forms were prepared using alcohol granulation technology. However, granulation technology is labor intensive and costly. In addition special procedures are necessary to address safety and environment issues involving the use of alcohol.

Accordingly, stable bupropion hydrochloride formulations prepared by safe, cost effective methods are greatly desired. The present invention provides such stable bupropion hydrochloride formulations.

DESCRIPTION OF THE INVENTION

In accordance with the present invention is provided a pharmaceutical composition comprising bupropion hydrochloride and a pharmaceutically acceptable stabilizer.

Bupropion Hydrochloride is described in U.S. Pat. Nos. 3,819,706 and 3,885,046 and the Merck Index, Twelfth Edition, entry no. 1523.

Stabilizer, as the term is used herein, means a compound which inhibits or prevents the degradation of bupropion hydrochloride so that it can be used in a pharmaceutical formulation while retaining much of its potency. Stabilizers useful in accordance with the present invention retain at least about 80% of the potency of bupropion hydrochloride and preferably over 90% of potency after one year of storage at room temperature (59–77° C.) at 35–60% humidity. Thus, a tablet containing 100 mg of bupropion hydrochloride should retain at least 80 mg and preferably more than 90 mg of bupropion hydrochloride at the end of 1 year in the presence of stabilizers of the present invention.

Suitable stabilizers have an aqueous suspension pH of from about 0.9 to about 4.0 at a concentration of about 6% w/w. Further, said stabilizers have solubility in water at 20° C. of less than about 10 g stabilizer/100 g water.

The stability of the formulation was tested in accordance with industry standards by storage for four to twelve weeks at about 40° C. and about 75% relative humidity. Formulations containing stabilizers of the present invention stored under these conditions retain at least 80% of the bupropion hydrochloride in the composition at the time of storage. In many instance formulations of the present invention retain more than 85% and ideally retain at least 90% of bupropion hydrochloride in the composition at the time of storage. Standard procedures such as HPLC may be used to determine the amount of active ingredient remaining after storage.

The aqueous suspension pH of the stabilizers of this invention is determined by adding 3.75 grams of stabilizer to 60 grams of deionized water in a Pyrex® beaker. The resulting mixture is stirred for approximately 5 minutes, using a stir plate and a magnetic stir bar. The resulting suspension or dispersion is examined using a Corning® pH Meter Model 355. Suspensions are stirred with a magnetic stir bar during analysis. Measurements are performed in duplicate and the average thereof is used.

Stabilizers of the present invention include dicarboxylic acids meeting the aforementioned criteria and more specifically include, but are not limited to, oxalic, succinic, adipic, fumaric and phthalic acids, or combinations thereof. Fumaric acid is a preferred stabilizer.

Pharmaceutical compositions of the present invention may optionally include any conventional ingredients for improving the physical properties, visual appearance or odor of the pharmaceutical. Examples include, but are not limited to, lubricants such as talc; binders such as starch, hydroxypropyl cellulose, hydroxypropyl methylcellulose and polyvinylpyrrolidone; diluents such as microcrystalline cellulose and lactose; disintegrants such as sodium starch glycolate, crospovidone and croscarmellose sodium; and colorants.

The total amount of inactive ingredient in the formulation, including the amount of stabilizer, is preferably more than 50% of the weight of bupropion hydrochloride in the composition and less than 650% of the weight of bupropion hydrochloride. The amount of stabilizer may be from about 10% to 100% of the weight of bupropion hydrochloride and is ideally about 10% to about 40% of the weight of bupropion hydrochloride in the composition. Most preferably, the amount of stabilizer is from about 15% to about 30% of the weight of bupropion hydrochloride. Furthermore about 1% to about 40% of the total weight of the tablet or capsule may be stabilizer. More preferably, stabilizer accounts for about 3% to about 6% of the total weight of the composition. The suitable amount of stabilizer is based on the label strength of bupropion hydrochloride in the pharmaceutical formulation in solid dosage form and can be determined by one skilled in the art.

Pharmaceutical compositions of the present invention generally contain 25 mg to 500 mg of bupropion hydrochloride. More preferred compositions of the invention contain 50 mg, 75 mg, 100 mg or 150 mg of active ingredient and may be in the form of tablets, caplets or capsules. Immediate release, modified release, and extended release profiles, or combinations thereof, are encompassed by the present invention.

Pharmaceutical compositions of the present invention are prepared by dry blending followed by direct compression. For instance, the ingredients are screened and blended in an industrial blender such as a Gemco® Double Cone Blender. The blended materials are milled such as with a Model D-6 Fitzmill®. Blending may be performed to achieve semi-geometric dilution. Thereafter, the ingredients are directly compressed into tablets using, for instance, a Kikusui Libra® tablet compression machine.

The following examples are illustrative, but are not limiting of the present invention. Throughout the examples, NF and USP are designations for standards published in the National Formulary and U.S. Pharmacopoeia, respectively.

EXAMPLES

Example 1

The formulation contained the following ingredients in the following amounts:

| Ingredient | Weight per Tablet (mg) 75 mg potency |
|---|---|
| Bupropion Hydrochloride | 75.0 |
| Cellulose, Microcrystalline, NF | 332.0 |
| Talc, USP | 23.0 |
| Fumaric Acid, NF | 18.0 |
| Hydroxypropyl Cellulose, EXF, NF | 10.0 |
| Coating | |
| Core Weight | 458.0 |
| Chromatone ® P DDB8361-W | 12.56 |
| Polyethylene Glycol 400, NF | 1.10 |
| Polysorbate 80, NF | 0.14 |
| Purified water USP | 0.1 mL |
| TOTAL | 471.8 |

The powder ingredients were weighed out for a 56,000 tablet batch size.

The following ingredients were sifted through a clean #20 mesh screen:

Cellulose, Microcrystalline, NF

Bupropion Hydrochloride

Hydroxypropyl Cellulose, EXF, NF

Fumaric Acid, NF

The screened material was transferred into a Gemco Double Cone Blender and blended for ten (10) minutes. Thereafter, the remaining Cellulose Microcrystalline NF was transferred into the Gemco Double Cone Blender and blended for ten (10) minutes. The blended material was milled through a Model D-6 Fitzmill equipped with a #1 plate, knives forward at medium speed. Talc, USP was passed through a #30 mesh screen into the milled material. The material was transferred into the Gemco Double Cone Blender and blended for ten (10) minutes. The blended material was compressed on a Kikusui Libra tablet compression machine at a weight of about 0.458 grams per tablet.

The coating solution was prepared as follows:

Purified water USP was added to a clean manufacturing tank equipped with a clean Mixer.

The following ingredients were added to the manufacturing tank:

Polyethylene Glycol 400, NF

Polysorbate 80, NF

The mixer was turned on.

Chromatone® P DDB8361-W was slowly added to the manufacturing tank. After the ingredients were added, the mixing was continued until a uniform suspension was achieved. The pan load amounts and solution amounts were calculated for solution application using the Hi Coater 60.

The tablet cores were loaded into the pan coater. The tablet bed was preheated until the exhaust air temperature was between 37° and 48° C. (approximately 43° C.). The pan speed was adjusted to approximately 8 RPM before starting the spray cycle. The spray cycle was activated. The exhaust temperature was maintained between 37° C. and 48° C. throughout the cycle. After the proper amount of solution was applied, the coated tablets were dried. Tablets were coated to an approximate weight gain of 24 mg per tablet.

Product stability data were obtained for this formulation stored for 12 weeks at 40° C., 75% relative humidity. Potency was determined using HPLC. Product stability data are presented in Table 1.

TABLE 1

| Weeks | Potency (%) |
|---|---|
| 0 | 99.9 |
| 4 | 97.1 |
| 12 | 95.8 |

Example 2

The formulation contained the following ingredients in the following amounts:

| Ingredient | Weight per Tablet (mg) 75 mg potency |
|---|---|
| Core | |
| Bupropion Hydrochloride | 75.0 |
| Cellulose, Microcrystalline, NF | 334.0 |
| Talc, USP | 23.0 |
| Fumaric Acid, NF | 18.0 |
| Hydroxypropyl Cellulose, EXF, NF | 10.0 |
| Core Weight | 460.0 |
| Coating | |
| Chromatone ® P DDB8440-OR | 12.56 |
| Polyethylene Glycol 400, NF | 1.10 |
| Polysorbate 80, NF | 0.14 |
| Purified water USP | 0.1 mL |
| TOTAL | 473.8 |

The powder ingredients were weighed out for a 500,000 tablet batch size.

The blended material was prepared as described in Example 1.

The blended material was then compressed on a Kikusui Libra tablet compression machine. Tablets were compressed at a weight of about 0.460 grams per tablet. Compression was performed in a room with temperature between 55°14 85° F. and low humidity (approximately 30% Relative Humidity).

The coating solution was prepared as follows:

Ninety-eight percent (98%) of purified water USP was added to a clean manufacturing tank equipped with a clean Chemineer Mixer with a four-inch blade. The Chemineer mixer was turned on and the setting was adjusted to 2–10 psi.

The following ingredients were added to the manufacturing tank:

Polyethylene Glycol 400, NF

Polysorbate 80, NF

After the ingredients were added, the mixer setting was adjusted to 1–4 psi to minimize foaming. The Polyethylene Glycol and Polysorbate 80, NF containers were rinsed using remaining 2% of Purified Water USP and the rinse water was added to the tank. Mixing was continued for approximately ten (10) minutes. The mixer setting was adjusted to 30–60 psi. Mixing was continued for approximately twenty (20) minutes.

Chromatone® P DDB8440-OR was added to the manufacturing tank. The mixer setting was reduced to 1–4 psi to reduce foaming and mixing continued for thirty (30) minutes. The pan load amounts and solution amounts were calculated for solution application using the Hi Coater 130.

The spray guns were installed in the pan coater unit as follows:

Spray Gun Nozzle Size: Air Cap 025-R, Liquid Nozzle 012.

Hi Coater 130:

Atomizing Air: 140 to 150 SLPM

Pattern Air: 190 to 200 SLPM

Four guns to equal 250–500 ml/min.

Solution was stirred with the mixer setting of 1–2 psi at all times.

The tablet cores were loaded into the pan coater. The tablet bed was preheated until the exhaust air temperature was between 37° C. and 48° C. (approximately 43° C.). The pan speed was adjusted to 5–9 RPM before starting the spray cycle. The spray cycle was activated. The exhaust temperature was maintained between 37° C. and 48° C. throughout the cycle. After the proper amount of solution was applied, the coated tablets were dried for approximately two (2) minutes. Steps were repeated for all pans to coat all tablets in the batch. All tablets were coated to an approximate weight gain of 13.8 mg per tablet.

Product stability data were obtained for this formulation stored for 12 weeks at 40° C., 75% relative humidity. Potency was determined using HPLC. Data are presented in Table 2.

TABLE 2

| Weeks | Potency (%) |
|---|---|
| 0 | 100.8 |
| 4 | 94.9 |
| 8 | 92.5 |
| 12 | 91.0 |

Example 3

The formulation contained the following ingredients in the following amounts:

| Ingredient | Weight per Tablet (mg) 100 mg potency |
|---|---|
| Bupropion Hydrochloride | 100.0 |
| Cellulose, Microcrystalline, NF | 442.0 |
| Talc, USP | 30.7 |
| Fumaric Acid, NF | 24.0 |
| Hydroxypropyl Cellulose, EXF, NF | 13.3 |
| Core Weight | 610.0 |
| Coating | |
| Chromatone ® P DDB8440-OR | 16.8 |
| Polyethylene Glycol 400, NF | 1.5 |
| Polysorbate 80, NF | 0.2 |
| Purified water USP | 0.14 mL |
| TOTAL | 628.5 |

The powder ingredients were weighed out for a 42,001 tablet batch size and prepared as described in Example 1. The blended material was compressed on a Kikusui Libra tablet compression machine at a weight of about 0.610 grams per tablet. Tablets were coated according to the procedure described in Example 1. Product stability data were obtained for this formulation stored for 12 weeks at 40° C., 75% relative humidity. Potency was determined using HPLC. Product stability data are presented in Table 3.

TABLE 3

| weeks | Potency (%) |
|---|---|
| 0 | 97.7 |
| 4 | 91.3 |
| 8 | 93.4 |
| 12 | 88.1 |

Example 4

The formulation contained the following ingredients in the following amounts:

| Ingredient | Weight per Tablet (mg) 100 mg potency |
|---|---|
| Core | |
| Bupropion Hydrochloride | 100.0 |
| Cellulose, Microcrystalline, NF | 445.0 |
| Talc, USP | 30.7 |
| Fumaric Acid, NF | 24.0 |
| Hydroxypropyl Cellulose, EXF, NF | 13.3 |
| Core Weight | 613.0 |
| Coating | |
| Chromatone ® P DDB8440-OR | 16.8 |
| Polyethylene Glycol 400, NF | 1.5 |
| Polysorbate 80, NF | 0.2 |
| Purified water USP | 0.14 mL |
| TOTAL | 631.5 |

The powder ingredients were weighed out for a 375,000 tablet batch size and prepared as described as in Example 2. Tablets were compressed at a compression weight of about 0.613 grams per tablet. Tablets were coated as described in Example 2 to an approximate weight gain of 18.5 mg per tablet.

Product stability data were obtained for this formulation stored for 12 weeks at 40° C., 75% relative humidity. Potency was determined using HPLC. Product stability data are presented in Table 4.

TABLE 4

| weeks | Potency (%) |
|---|---|
| 0 | 98.7 |
| 4 | 94.4 |
| 8 | 93.9 |
| 12 | 92.1 |

Example 5

The formulation contained the following ingredients in the following amounts:

| Ingredient | Weight per Tablet (mg) 75 mg potency |
|---|---|
| Bupropion Hydrochloride | 75.0 |
| Cellulose, Microcrystalline, NF | 332.0 |
| Talc, USP | 23.0 |

-continued

| Ingredient | Weight per Tablet (mg) 75 mg potency |
|---|---|
| Fumaric Acid, NF | 18.0 |
| Hydroxypropyl Cellulose, EXF, NF | 10.0 |
| TOTAL | 458.0 |

The powder ingredients were weighed out for a 45,000 tablet batch size. The composition was prepared as described in Example 1. Tablets were compressed at a compression weight of about 0.458 grams per tablet. Tablets were film coated as described in Example 2 to an approximate weight gain of 4.25% (19.5 mg).

Product stability data were obtained for this formulation stored for 12 weeks at 40° C., 75% relative humidity. Potency was determined using HPLC. The following product stability data shown in Table 5 were obtained for this formulation.

TABLE 5

| Weeks | Potency (%) |
|---|---|
| 0 | 98.5 |
| 4 | 95.0 |
| 8 | 93.0 |
| 12 | 89.8 |

What is claimed is:

1. A method for preparing a stable composition of bupropion hydrochloride in solid form comprising:
   dry blending bupropion hydrochloride and solid stabilizer to equally distribute the components;
   dry milling the blended material; and
   preparing a solid dosage form.

2. The method of claim 1 wherein the stabilizer is fumaric acid.

* * * * *